United States Patent [19]
Hughes et al.

[11] Patent Number: 5,798,556
[45] Date of Patent: Aug. 25, 1998

[54] SENSOR AND METHOD OF FABRICATION

[75] Inventors: Henry G. Hughes, Scottsdale; Marilyn J. Stuckey; Margret L. Kniffin, both of Tempe; Ping-chang Lue, Scottsdale, all of Ariz.

[73] Assignee: Motorola, Inc., Schaumburg, Ill.

[21] Appl. No.: 620,729

[22] Filed: Mar. 25, 1996

[51] Int. Cl.$^6$ .......................... H01L 27/14; H01L 29/82; H01L 29/84
[52] U.S. Cl. .......................... 257/414
[58] Field of Search .......................... 257/414

[56] References Cited

U.S. PATENT DOCUMENTS

| | | |
|---|---|---|
| 4,592,824 | 6/1986 | Smith et al. . |
| 4,671,852 | 6/1987 | Pyke . |
| 4,768,070 | 8/1988 | Takizawa et al. . |
| 4,801,380 | 1/1989 | Parker et al. . |
| 4,874,500 | 10/1989 | Madou et al. . |
| 5,204,690 | 4/1993 | Lorenze, Jr. et al. . |
| 5,323,051 | 6/1994 | Adams et al. . |

FOREIGN PATENT DOCUMENTS

| | | |
|---|---|---|
| 3029153 | 3/1982 | Germany . |
| 4439286 | 5/1996 | Germany . |
| 9513860 | 5/1995 | WIPO . |

OTHER PUBLICATIONS

Patent Abstracts of Japan, vol. 095, 31 Oct. 1995 & JP 07 140103 S (Seiko Epson Corp), 2 Jun. 1995.
Patent Abstracts of Japan, vol. 010, No. 389 (P-531), 26 Dec. 1986 & JP 61 178653 A (Matsuhits Electric Works LTD), 11 Aug. 1986.

*Primary Examiner*—Stephen Meier
*Attorney, Agent, or Firm*—George C. Chen

[57] ABSTRACT

A sensor (10) includes a cavity (31) formed by a substrate (11), an adhesive (21), and a filter (22). A sensing element (14) is located inside the cavity (31) while electrical contacts (17, 18) coupled to the sensing element (14) are located outside the cavity (31). The filter (22) protects the sensing element (14) from physical damage and contamination during die singulation and other assembly processes. The filter (22) also improves the chemical sensitivity, selectivity, response times, and refresh times of the sensing element (14).

19 Claims, 1 Drawing Sheet

SENSOR AND METHOD OF FABRICATION

BACKGROUND OF THE INVENTION

This invention relates, in general, to semiconductor devices, and more particularly, to sensors.

The packaging process for sensors is labor intensive, time consuming, and expensive. For chemical sensors, the packaging process includes sawing a semiconductor substrate into individual chemical sensor chips. Then, the individual chemical sensor chips are separately bonded to and assembled in a bulky metal package known in the art as a T39 package or a T05 package. An example of a T05 package is described in U.S. Pat. No. 4,768,070, issued to Takizawa et al. on Aug. 30, 1988. This piece-part packaging process is slow and tedious and requires careful handling of the individual chemical sensor chips, which may become contaminated and physically damaged during the packaging process.

Accordingly, a need exists for a sensor that is packaged using a batch processing technique that improves throughput and reduces cycle time for fabricating and packaging a sensor. The wafer-level batch packaging technique should produce a packaged sensor that is compact in size and should also protect each sensor chip from contamination and physical damage during subsequent handling.

DETAILED DESCRIPTION OF THE DRAWINGS

Figure 1:
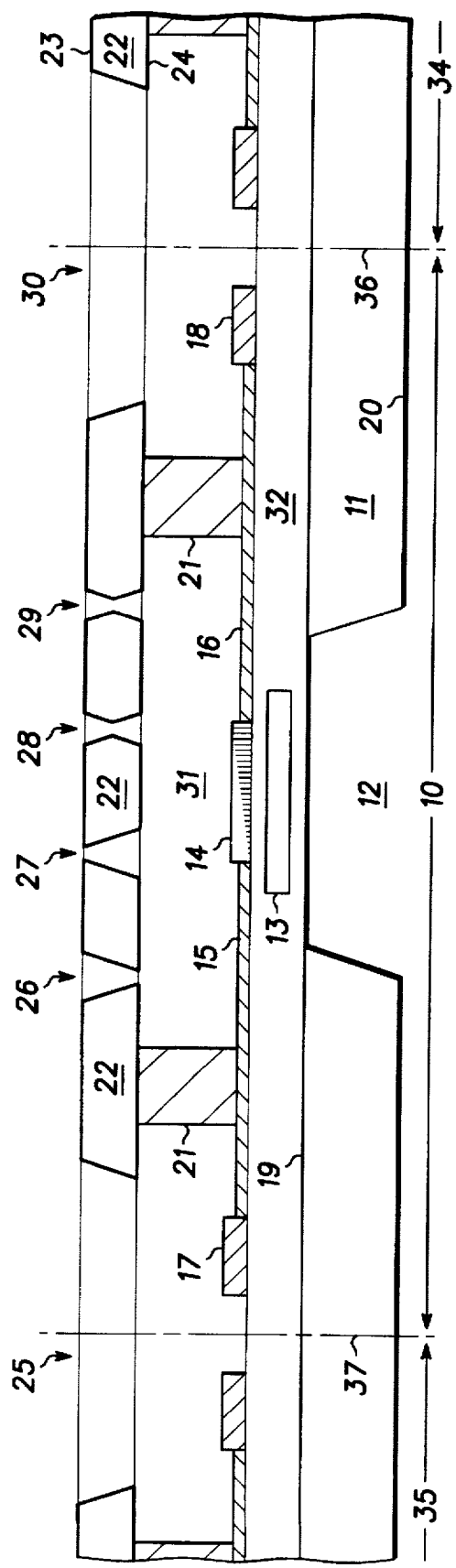
FIG. 1 illustrates a cross-sectional view of an embodiment of a sensor in accordance with the present invention.

Turning to the figures for a more detailed description, FIG. 1 illustrates a cross-sectional view of an embodiment of a sensor 10. Sensor 10 is a semiconductor component that includes a substrate 11. Substrate 11 has a surface 19 opposite a surface 20 and is typically comprised of a semiconductor material such as, for example, silicon, a III-V compound semiconductor, or a II-VI compound semiconductor.

It is understood that a plurality of sensors can be fabricated on substrate 11. For example, FIG. 1 depicts portions of sensors 34 and 35 on substrate 11 and adjacent to sensor 10. FIG. 1 also portrays lines 36 and 37, which serve as scribe lines for singulating sensor 10 apart from sensors 34 and 35, respectively.

An electrically insulating layer 32 is provided over surface 19 of substrate 11. Electrically insulating layer 32 is preferably a dielectric material such as, for example, silicon oxide or silicon nitride and can be deposited overlying substrate 11 using techniques known in the art.

Substrate 11 has an optional recess 12 formed in a portion of surface 20 to facilitate heat dissipation in sensor 10 as described hereinafter. Recess 12 extends from surface 20 toward surface 19 and can expose a portion of electrically insulating layer 32. To ensure a manufacturable process for sensor 10, recess 12 is preferably etched into surface 20 using an anisotropic etchant that etches along specific crystal planes of substrate 11. The anisotropic etchant should not significantly etch electrically insulating layer 32 compared to substrate 11. Examples of anisotropic etchants that are suitable for use with single crystal silicon substrates include, but are not limited to, potassium hydroxide, ammonium hydroxide, cesium hydroxide, hydrazine, ethylenediamine/pyrocatechol, and tetramethylammonium hydroxide.

Sensor 10 also includes a sensing element 14, which is supported by electrically insulating layer 32 and substrate 11 and which overlies recess 12. When sensor 10 is a chemical sensor, sensing element 14 is typically a resistor whose resistance changes upon exposure to a specific liquid or gas (not shown). At elevated operating temperatures, the resistivity of sensing element 14 is typically about 1 kiloohm–50 megaohms. As known in the art of chemical sensors, the presence of a specific liquid or gas is transformed from a chemical reaction into an electrical signal by a sensor. As an example, a control circuit (not shown) can detect a change in the resistivity of sensing element 14 by measuring a change in a current or voltage drop across sensing element 14. The control circuitry can be located on a different substrate or can be fabricated in substrate 11 to create an integrated chemical sensor system.

Sensing element 14 is provided or formed over electrically insulating layer 32 and surface 19 of substrate 11 using techniques known in the art. When sensor 10 is a chemical sensor, sensing element 14 is comprised of an electrically conductive and chemically sensitive film including, but not limited to, metal oxides, transition metals, or noble metals. For example, sensing element 14 can be comprised of tin oxide, zinc oxide, titanium oxide, or an alloy of platinum and gold. Different compositions of sensing element 14 permit the sensing or monitoring of different liquids or gases. It is understood that the material used for sensing element 14 can be doped to further improve the chemical sensitivity and selectivity of sensing element 14 and sensor 10.

Sensing element 14 can be heated by an optional heating element 13 to help catalyze a chemical reaction between sensing element 14 and the desired liquid or gas. Heating element 13 is formed using techniques known to those skilled in the art. As an example, heating element 13 can be comprised of polysilicon or a metal such as platinum, gold, or the like.

As illustrated in FIG. 1, heating element 13 is located within electrically insulating layer 32, overlies recess 12, and underlies sensing element 14. It is understood that heating element 13 can be located on a different substrate than substrate 11. However, it is desirable for both heating element 13 and sensing element 14 to be located on substrate 11 for efficient heating and space conservation. Recess 12 in substrate 11 assists the heat dissipation or cooling of heating element 13 and sensor 10.

Coupling lines 15 and 16 electrically couple features 17 and 18, respectively, to sensing element 14.

Coupling lines 15 and 16 are comprised of an electrically conductive material such as, for example, a silicide or a metal. Coupling lines 15 and 16 are formed overlying electrically insulating layer 32 and surface 19 of substrate 11 using techniques known in the art.

Features 17 and 18 provide electrical contacts for sensing element 14. For instance, assembly wire-bond wires can be coupled to features 17 and 18, which can serve as bonding pads. Features 17 and 18 are typically comprised of a metal including, but not limited to, gold or copper and are deposited overlying electrically insulating layer 32 and surface 19 of substrate 11 using sputtering, electroplating, chemical vapor deposition, or evaporation techniques.

An adhesive 21 overlies coupling lines 15 and 16, overlies electrically insulating layer 32, overlies surface 19 of substrate 11, and is preferably spatially separated from sensing element 14 to avoid contaminating sensing element 14. Adhesive 21 can be any appropriate organic or inorganic bonding material such as, for example, a solder preform, a silk-screened epoxy, or fritted glass. If an electrically conductive adhesive is used for adhesive 21, an insulating layer (not shown) should electrically isolate coupling lines 15 and 16 from adhesive 21.

Adhesive 21 couples or adheres electrically insulating layer 32 and a mesh, screen, or filter 22 in order to cap or package sensor 10. As a result, adhesive 21, electrically insulating layer 32, substrate 11, and filter 22 form a cavity 31. The volume of cavity 31 can be controlled by the thickness or height of adhesive 21. As illustrated in FIG. 1, sensing element 14 is located inside cavity 31, and features 17 and 18 are located outside cavity 31.

Filter 22 is provided over electrically insulating layer 32 and cavity 31 to filter, screen out, or prevent undesirable particles or chemicals from entering cavity 31. Filter 22 has a surface 23, an opposite surface 24, contact openings 25 and 30, and filtering holes 26, 27, 28, and 29 that serve as a filtering mechanism for filter 22 as discussed in more detail hereinafter.

Filter 22 is preferably spatially separated from sensing element 14 to avoid contaminating or damaging sensing element 14. Filter 22 should have an appropriate thickness such that filter 22 is substantially rigid in order to prevent an elastic deformation of filter 22, in which filter 22 can contact and damage sensing element 14.

A wide variety of materials can be used for filter 22 as discussed hereinafter. However, many of the materials used for filter 22 may outgas a chemical at the elevated operating temperatures of sensor 10. Preferably, filter 22 is devoid of outgassing a chemical at the elevated operating temperatures to ensure an accurate chemical response of sensor 10 to the ambient. However, if filter 22 does outgas a chemical, filter 22 should not outgas a chemical that is capable of being detected by sensing element 14 in order to ensure accurate environmental monitoring for sensor 10. Similarly, adhesive 21, electrically insulating layer 32, substrate 11, coupling lines 15 and 16, and features 17 and 18 should also not outgas a chemical that can be sensed by sensing element 14 at the operating temperatures of sensor 10.

Filter 22 can be comprised of a non-porous material or a porous or gas permeable material. Examples of potentially suitable non-porous materials include, but are not limited to, conventional single crystal silicon substrates, III-V compound semiconductor substrates, and II-VI compound semiconductor substrates. Examples of potentially suitable porous or gas permeable materials include, but are not limited to, porous silicon substrates, polymer membranes, porous ceramic, glass, charcoal filters, thermosets, alumina, polyimides, silica, and quartz.

When filter 22 is comprised of a porous or gas permeable material, filter 22 has an additional filtering mechanism that filter 22 does not have when comprised of a non-porous material. Certain liquids or gases can penetrate through certain porous or gas permeable materials and can enter cavity 31 without passing through filtering holes 26, 27, 28, or 29 of filter 22. Thus, a porous or gas permeable material can extend or enhance the filtering capabilities of filter 22 over that of a non-porous material in order to improve the chemical sensitivity and selectivity of sensor 10.

Each porous or gas permeable material can have a different pore size that can be used to filter out different sizes of particles, chemicals, or molecules. The porous or gas permeable materials can be chemically active. As a specific example of a chemically active gas permeable material, a layer of a metallophthalocyanine polymer can be used for filter 22 in order to prevent nitrous oxide from passing into cavity 31. As a specific example of a porous material, a compressed charcoal filter can be used for filter 22 to filter out and prevent hydrocarbons from entering cavity 31. Furthermore, a polyimide layer can be used for filter 22 to filter out and prevent moisture or water vapor from entering cavity 31.

Referring back to the description of contact openings 25 and 30 within filter 22, contact openings 25 and 30 are located over and permit access to features 17 and 18, respectively. When features 17 and 18 serve as bonding pads, contact openings 25 and 30 each have a dimension of approximately 50–1,000 microns to enable assembly wirebond wires to extend through contact openings 25 and 30 to contact features 17 and 18, respectively. Contact openings 25 and 30 can also expose die singulation areas, identified as lines 36 and 37 in FIG. 1.

Filtering holes 26, 27, 28, and 29 of filter 22 are located over cavity 31 and serve as a filtering mechanism for filter 22. While filter 22 can have a single hole overlying cavity 31, filter 22 preferably has a plurality of holes to permit adequate gas or liquid flow into and out of cavity 31 while maintaining adequate filtering functionality as described hereinafter. Filtering holes 26, 27, 28, and 29 each preferably have a diameter smaller than that of contact openings 25 and 30 to prevent unwanted particles from entering cavity 31. Thus, filter 22 protects sensing element 14 from physical damage and contamination during substrate dicing, other assembly processes, and operation of sensor 10.

If desired, filtering holes 26, 27, 28, and 29 can each have a diameter on the order of angstroms to microns in order to prevent larger sized molecules or chemicals from entering cavity 31 and chemically reacting with sensing element 14. In this manner, filter 22 is also used as a chemical filter to improve the chemical selectivity and sensitivity of sensor 10. As an example, assume that sensor 10 should only monitor small hydrocarbon molecules but that sensing element 14 chemically reacts with small hydrocarbon molecules, larger protein molecules, and even larger deoxyribonucleic acid molecules (DNA). In this example, if filtering holes 26, 27, 28, and 29 each had a diameter on the order of a few angstroms, small hydrocarbon molecules can pass through filtering holes 26, 27, 28, and 29 to react with sensing element 14 while the larger protein molecules and the DNA molecules cannot pass through filtering holes 26, 27, 28, and 29 and cannot react with sensing element 14. Thus, in this example, the chemical selectivity of sensor 10 is improved.

Filtering holes 26, 27, 28, and 29 and contact openings 25 and 30 are micromachined into filter 22 prior to coupling together filter 22 and substrate 11. Filtering holes 26, 27, 28, and 29 and contact openings 25 and 30 can be formed using a variety of different chemical and physical methods. For example, a reactive ion etch or a mechanical drilling technique can be used to form filtering holes 26, 27, 28, and 29 and contact openings 25 and 30 in filter 22. As another example, when filter 22 is comprised of a non-porous single crystal silicon substrate having a thickness of approximately 100–500 microns, an anisotropic etchant similar to that used for recess 12 in substrate 11 can also be used to etch filtering holes 26, 27, 28, and 29 and contact openings 25 and 30.

Filtering holes 26, 27, 28, and 29 and contact openings 25 and 30 can be etched from surface 23, from surface 24, or from both surfaces 23 and 24. As illustrated in FIG. 1, contact openings 25 and 30 and filtering hole 26 are etched from surface 23; hole 27 is etched from surface 24; and holes 28 and 29 are etched from surfaces 23 and 24. When holes are etched from both surfaces 23 and 24, a greater number or a higher density of holes can be provided in filter 22 compared to when the holes are only etched from a single surface of filter 22.

Figure 2:
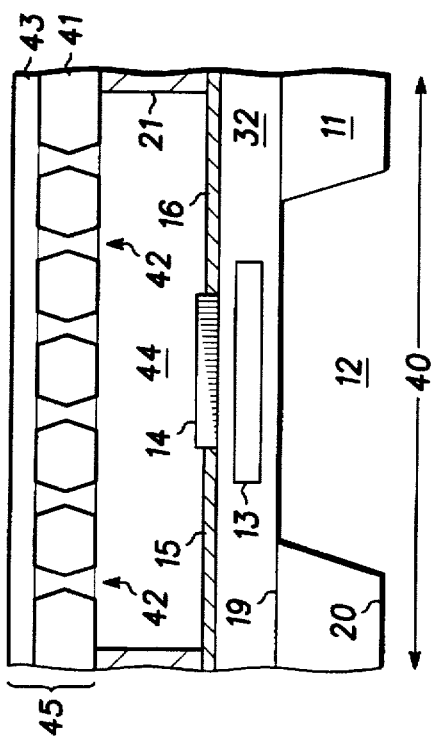
FIG. 2 portrays a partial cross-sectional view of an alternative embodiment of the sensor of FIG. 1 in accordance with the present invention.

Continuing with FIG. 2, a partial cross-sectional view of an alternative embodiment of sensor 10 in FIG. 1 is portrayed as a sensor 40. Sensor 40 of FIG. 2 is similar to sensor 10 of FIG. 1, wherein the same reference numerals are used in FIGS. 1 and 2 to denote the same elements. In FIG. 2, a cavity 44 is formed by using adhesive 21 to couple together electrically insulating layer 32 and a filter 45. Cavity 44 and filter 45 are similar in purpose to cavity 31 and filter 22, respectively, of FIG. 1.

Filter 45 is comprised of a layer 43 overlying a support layer 41. Support layer 41 is similar in composition to filter 22 of FIG. 1. Support layer 41 has a plurality of holes 42, which are covered by layer 43 and which are similar in purpose to filtering holes 26, 27, 28, and 29 of filter 22 in FIG. 1.

Layer 43 is comprised of a porous or gas permeable material that serves as a selective filter to permit certain chemicals to pass through and to restrict the passage of other chemicals. Examples of porous materials and gas permeable materials suitable for layer 43 have previously been described herein.

Layer 43 can be sputtered, sprayed, laminated, dispensed, or painted to a thickness of approximately 0.1–30 microns over support layer 41 after coupling support layer 41 to electrically insulating layer 32. Alternatively, layer 43 can be provided over support layer 41 before filter 45 is attached to electrically insulating layer 32. In this alternative process, filter 45 can be coupled to electrically insulating layer 32 such that electrically insulating layer 32 and substrate 11 are located closer to layer 43 than support layer 41, which is a configuration that is not shown in FIG. 2. However, filter 45 is preferably coupled to electrically insulating layer 32 such that electrically insulating layer 32 and substrate 11 are located closer to support layer 41 than layer 43, as portrayed in FIG. 2, so that plurality of holes 42 will not become clogged during the operation of sensor 40.

Figure 3:
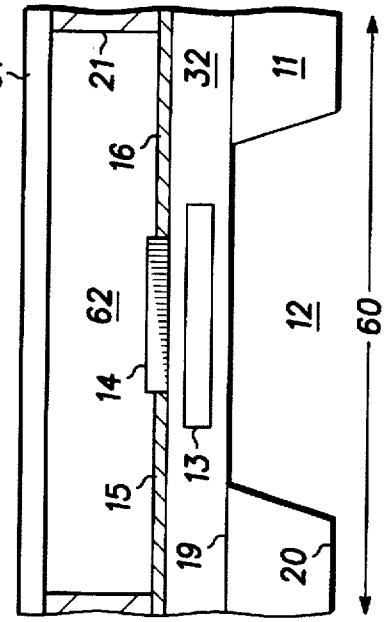
FIG. 3 depicts a partial cross-sectional view of another alternative embodiment of the sensor of FIG. 1 in accordance with the present invention.

Referring now to FIG. 3, a partial cross-sectional view of another alternative embodiment of sensor 10 in FIG. 1 is depicted as a sensor 60. Sensor 60 of FIG. 3 is also similar to sensor 10 of FIG. 1, wherein the same reference numerals are used in FIGS. 1 and 3 to denote the same elements. In FIG. 3, adhesive 21 couples together electrically insulating layer 32 and a filter 61 to form a cavity 62 therebetween. Cavity 62 and filter 61 are similar in purpose to cavity 31 and filter 22, respectively, in FIG. 1.

Filter 61 is comprised of a porous or gas permeable material that has an appropriate thickness to provide substantial rigidity in order to prevent damaging sensing element 14 as previously discussed herein. Unlike filter 22 of FIG. 1, filter 61 of FIG. 3 does not have any filtering holes. Filter 61 can be similar in composition to layer 43 of FIG. 2 and can have a thickness of approximately 50–500 microns.

Sensors 10, 40, and 60 in FIGS. 1, 2, and 3, respectively, have several advantages over prior art sensors that are packaged in conventional metal T05 or T39 packages. For example, cavities 31, 44, and 62 of FIGS. 1, 2, and 3, respectively, have smaller cavity volumes compared to the cavities or enclosed regions of the conventional metal T05 or T39 packages. With smaller cavity volumes, sensors 10, 40, and 60 are smaller in size and more compact than the conventional metal T05 or T39 packages, which conserves space in any application. Sensors 10, 40, and 60 are at least approximately one hundred times smaller than the conventional metal T05 or T39 packages.

Also, with smaller cavity volumes, cavities 31, 44 and 62 can be filled more quickly with a critical concentration of a chemical to be sensed by sensing element 14. A smaller cavity volume also permits faster purging of a critical chemical concentration. Thus, the response and refresh times for sensors 10, 40, and 60 are improved over the prior art. As discussed previously, the cavity volumes of cavities 31, 44, and 62 can be controlled by the thickness or height of adhesive 21. The minimum cavity volume required for cavities 31, 44, and 62 is dependent upon the composition and operating temperatures of sensing element 14, the particular chemical being sensed, and the diffusion rate of an ambient gas or liquid into and out of cavities 31, 44, and 62.

Furthermore, the manufacturing process for sensors 10, 40, and 60 is less time consuming, less expensive, and less labor intensive compared to the prior art. When substrate 11 and filters 22, 45 or 61 are portions of different semiconductor wafers, the fabrication of sensor 10 can be accomplished by using automated semiconductor wafer handling equipment, which reduces human intervention and improves manufacturing yields. In this manner, the fabrication of sensor 10 is compatible with high volume, production environments.

Thus, sensors 10, 40, and 60 can be packaged or assembled using a wafer-level batch process, wherein hundreds or thousands of sensors are simultaneously packaged on a single semiconductor substrate before the individual sensors are singulated. This wafer-level batch packaging process improves throughput and is more cost effective than the manual and tedious prior art process of separately packaging one sensor at a time.

Moreover, the wafer-level packaging protects sensing element 14 from being damaged during die singulation because sensing element 14 is enclosed within cavity 31, 44, or 62 prior to the singulation process. Additionally, adhesive 21 and filters 22, 45, and 61 stiffen and strengthen sensors 10, 40, and 60, respectively, which lowers the potential for breakage. Accordingly, the manufacturing yields for sensors 10, 40, and 60 are further improved over the prior art.

Therefore, in accordance with the present invention, it is apparent there has been provided an improved sensor that overcomes the disadvantages of the prior art. The inefficient, piece-part assembly of sensors in conventional metal T05 and T39 packages is eliminated, and a cost-effective and cycle time reducing method improves the mechanical strength and manufacturing yields for fabricating a sensor. The size of the packaged sensor is reduced by a factor of greater than approximately one hundred compared to conventionally packaged sensors. Furthermore, the performance of a sensor is enhanced by improving chemical sensitivity, chemical selectivity, and refresh and response times.

While the invention has been particularly shown and described with reference to preferred embodiments, it will be understood by those skilled in the art that changes in form and detail may be made without departing from the spirit and scope of the invention. For instance, humidity and temperature sensors can be included within cavities 31, 44, and 62 to improve the monitoring capabilities of sensors 10, 40, and 60, respectively. Furthermore, the process described herein can be applied to packaging other types of sensors such as, for example, chemical field effect transistors (CHEMFETs), surface acoustic wave (SAW) devices, capacitive sensors. Accordingly, the disclosure of the present invention is not intended to be limiting. Instead, the disclosure of the present invention is intended to be illustrative of the scope of the invention, which is set forth in the following claims.

We claim:

1. A sensor comprising:
   a substrate having a recess;
   a sensing element overlying the substrate, the sensing element located outside of the recess;
   a filter overlying the sensing element wherein the filter is electrically unbiased; and
   an adhesive coupling the substrate and the filter.

2. The sensor according to claim 1 wherein the sensing element is spatially separated from the adhesive and the filter.

3. The sensor according to claim 1 wherein the sensing element includes a chemically sensitive film and wherein the substrate has a recess underlying the chemically sensitive film.

4. The sensor according to claim 3, wherein the substrate, the filter, and the adhesive are comprised of materials substantially devoid of outgassing a chemical sensed by the chemically sensitive film during operation of the sensor.

5. The sensor according to claim 1 wherein the filter is comprised of a material selected from the group consisting essentially of gas permeable materials, porous materials, or non-porous materials.

6. The sensor according to claim 1 wherein the filter includes a semiconductor substrate having a plurality of holes.

7. The sensor according to claim 6 wherein the filter includes a material overlying the plurality of holes, the material selected from the group consisting essentially of porous materials or gas permeable materials.

8. The sensor according to claim 1 wherein the substrate, filter, and adhesive create a cavity, wherein the substrate forms a bottom surface of the cavity and wherein the filter forms a top surface of the cavity and wherein the adhesive forms a side wall of the cavity the sensing element located inside the cavity, wherein the sensor further comprises an electrical contact electrically coupled to the sensing element, the electrical contact located outside the cavity.

9. The sensor of claim 1 wherein the substrate comprises:
   a support substrate having the recess;
   an electrically insulative layer between the sensing element and the support substrate; and
   a heating element between a portion of the electrically insulative layer and the support substrate.

10. A semiconductor component comprising:
    a chemically sensitive film;
    a filter overlying and spatially separated from the chemically sensitive film, the filter devoid of electrical biasing;
    a support substrate underlying the chemically sensitive film, the support substrate comprised of a semiconductor substrate and an electrically insulative layer, the electrically insulative layer located between the semiconductor substrate and the chemically sensitive film; and
    an adhesive coupling the filter and the support substrate.

11. The semiconductor component according to claim 10 wherein the filter includes a semiconductor substrate.

12. The semiconductor component according to claim 11 wherein the filter includes a material overlying the semiconductor substrate of the filter, the semiconductor substrate of the filter having a plurality of holes, the material covering the plurality of holes, and the material selected from the group consisting essentially of porous materials or gas permeable materials.

13. The semiconductor component according to claim 10 wherein the filter is penetrable by a first chemical, wherein the filter filters out a second chemical, and wherein the first and second chemicals are chemically reactive with the chemically sensitive film.

14. The semiconductor component of claim 10 wherein the support substrate further comprises a heater located within the electrically insulative layer and electrically isolated from the chemically sensitive film and the semiconductor substrate by the electrically insulative layer.

15. A semiconductor device comprising:
    a semiconductor substrate having a first surface, a second surface opposite the first surface, and a recess in the first surface;
    an electrically insulative layer overlying the second surface of the semiconductor substrate;
    a chemical sensing element overlying the electrically insulative layer and the recess, the chemical sensing element devoid of being located within the recess;
    a filtering layer overlying and physically separated from the chemical sensing element, the filtering layer electrically insulated from all electrically conductive layers of the semiconductor device;
    an adhesive coupling the electrically insulative layer to the filtering layer; and
    a heating element underlying the chemical sensing element to heat the chemical sensing element.

16. The semiconductor device of claim 15 further comprising bonding pads overlying the electrically insulative layer and electrically coupled to the chemical sensing element.

17. The semiconductor device of claim 16 wherein the filtering layer has holes overlying the bonding pads and wherein the heating element is electrically isolated from the chemical sensing element.

18. The semiconductor device of claim 17 wherein the filtering layer comprises a layer of a material selected from the group consisting essentially of a porous material or a gas permeable material, the layer of the material overlying the chemical sensing element.

19. The semiconductor device of claim 18 wherein the filtering layer further comprises a layer of a material having holes overlying the chemical sensing element.

* * * * *